US00PP16353P3

(12) United States Plant Patent
Eremin

(10) Patent No.: US PP16,353 P3
(45) Date of Patent: Mar. 21, 2006

(54) ***PRUNUS* ROOTSTOCK NAMED 'ELTA'**

(50) Latin Name: ***Prunus* sp.**
Varietal Denomination: Elta

(75) Inventor: Gennadiy Eremin, Krasnodar (RU)

(73) Assignee: Varieties International, LLC, Lafayette, OR (US)

( * ) Notice: Subject to any disclaimer, the term of this patent is extended or adjusted under 35 U.S.C. 154(b) by 143 days.

(21) Appl. No.: 10/802,633

(22) Filed: Mar. 17, 2004

(65) Prior Publication Data

US 2005/0210554 P1 Sep. 22, 2005

(51) Int. Cl.
*A01H 5/00* (2006.01)

(52) U.S. Cl. ..... Plt./180
(58) Field of Classification Search ..... Plt./183, Plt./180
See application file for complete search history.

(56) References Cited

U.S. PATENT DOCUMENTS

2003/0217400 P1 * 11/2003 Eremin ..... Plt./183

* cited by examiner

*Primary Examiner*—Kent Bell
*Assistant Examiner*—W. C. Haas
(74) *Attorney, Agent, or Firm*—The Webb Law Firm

(57) ABSTRACT

A new and distinct *Prunus* sp. plant used as a rootstock that exhibits desirable propagation characteristics and light pink flowers.

3 Drawing Sheets

Botanical classification: *Prunus* sp.
Varietal denomination: 'Elta'.

BACKGROUND OF THE INVENTION

The present invention comprises a new and distinct cultivar of *Prunus* sp. used as a rootstock known by the varietal name 'Elta'. The new variety was discovered in the Krasnodar region of Russia around 1987. The new variety is the result of free pollination of a *Prunus lannesiana* plant (female parent). The purpose of breeding 'Elta' was to provide a productive clonal rootstock for cherry varieties. The new variety has been trial and field tested and has been found to retain its distinctive characteristics and remain true to type through successive propagations. The following characteristics distinguish 'Elta' from other varieties known to the breeder:

1. 'Elta' has big stipules;
2. 'Elta' is easy to propagate via green cuttings; and
3. 'Elta' has light pink flowers in bunches.

DESCRIPTION OF THE DRAWINGS

The accompanying photographic drawings illustrate the new variety, with the color being as nearly true as is possible with color illustrations of this type.

DETAILED BOTANICAL DESCRIPTION

Figure 1:
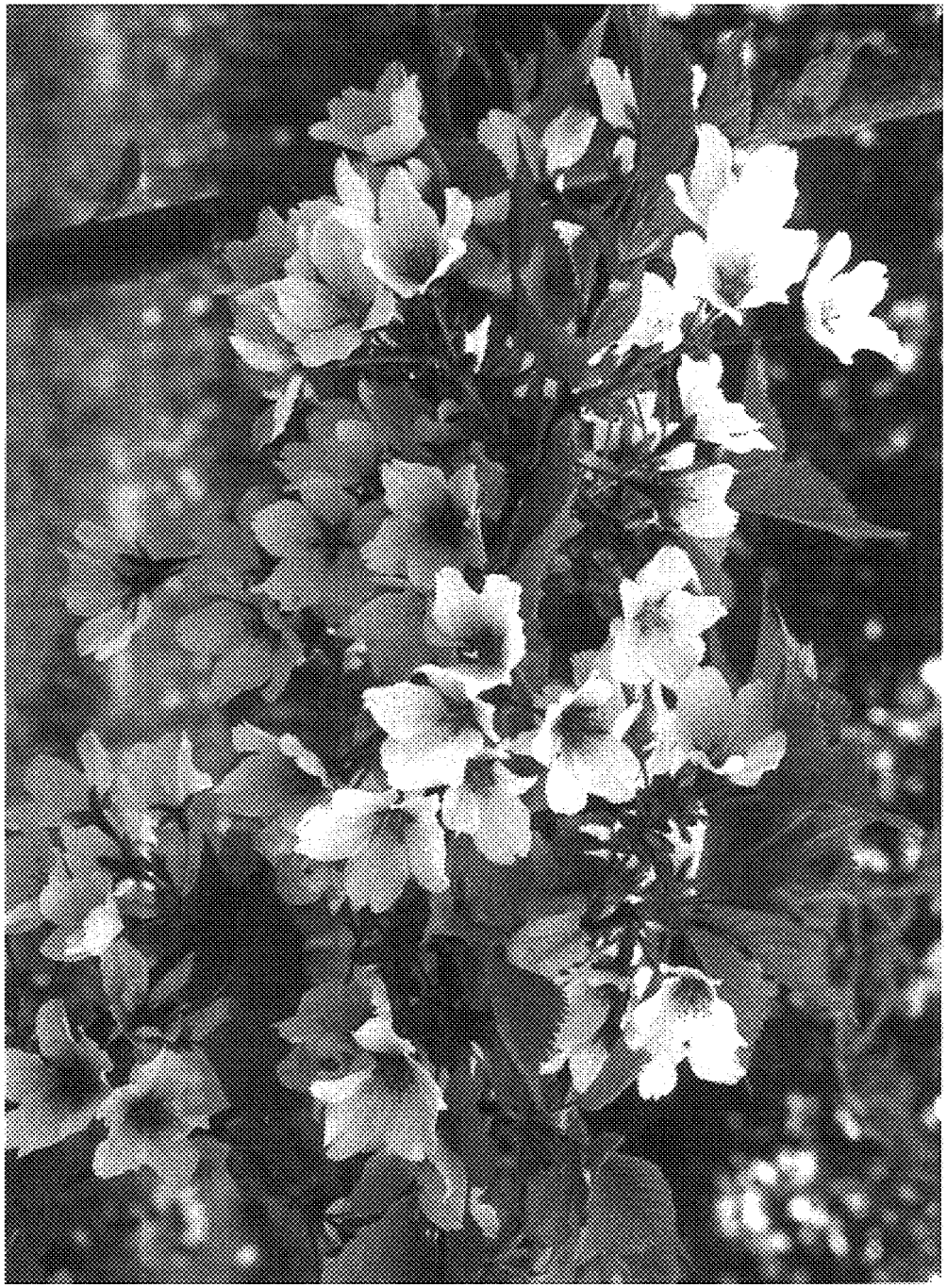
FIG. 1 shows a close-up view of the flowers of the new variety.
Figure 2:
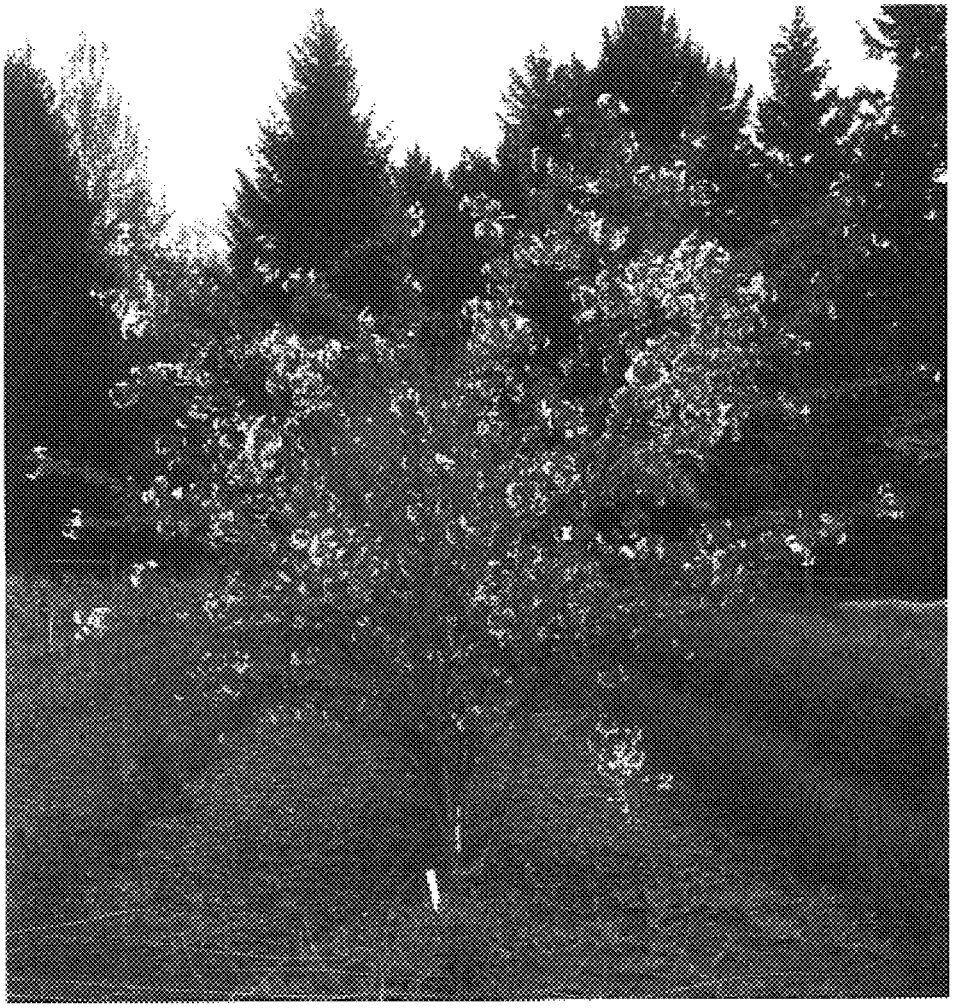
FIG. 2 shows the new variety grown to a flowering plant.
Figure 3:
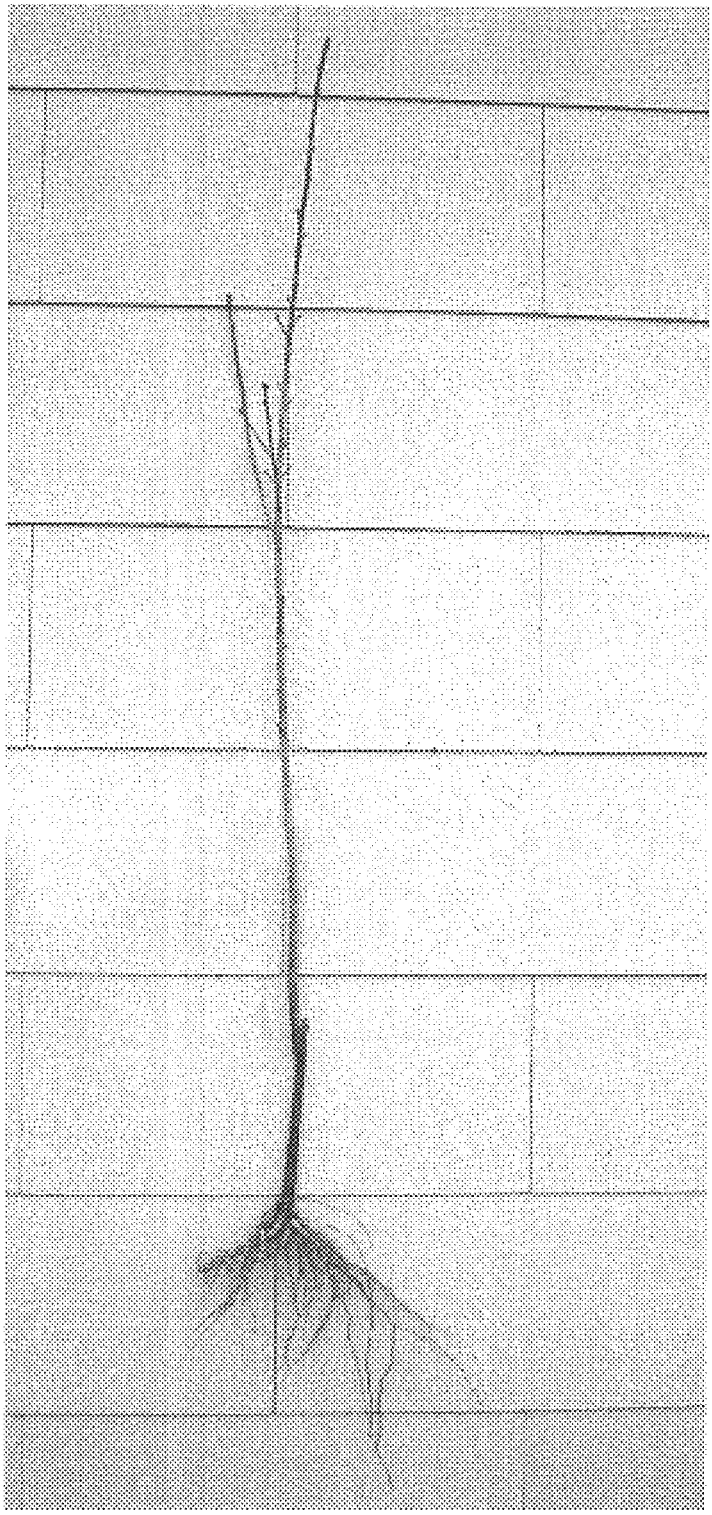
FIG. 3 illustrates the roots and branches of the new variety.

The following detailed description sets forth the characteristics of the new cultivar. The data which defines these characteristics were collected from plants produced by asexual reproductions via green cuttings, and grown on their own roots, carried out in the Krasnodar Region of Russia. The new variety was grown under warm, dry Summer conditions with a temperature range of 70° F. to 105° F. The Winter months are mild with lows to −10° F. The Spring and Fall months are humid. The color readings were taken in natural daylight.

Tree
Use: Rootstock.
Fruit bearing: Promotes high productivity of grafted scion.
Size (generally): Medium.
Height at 4 years: 8 feet.
Spread at 4 years: 5 feet.
Form: Rounded.
Trunk:
- *Size*.—Medium.
- *Bark color*.—187A.
- *Diameter*.—23.0 mm at 4 years when grown in a pot.
- *Texture*.—Smooth.
- *Lenticel number*.—6.0 to 15.0 per $cm^2$ at 4 years.

Branches:
- *Surface texture*.—Smooth.
- *Young bark color*.—184C.
- *Mature bark color*.—187C.
- *Internode length*.—2.3 cm to 3.0 cm.
- *Lenticel shape*.—Round.
- *Lenticel number*.—2.0 to 5.0 per $cm^2$ on a 1 year old branch.
- *Lenticel size*.—1 mm.
- *Leaf bud shape*.—Conical.
- *Leaf bud size*.—6.0 mm. in length.
- *Branch diameter*.—5.0 mm at 1 year.
- *Crotch angle*.—30° to 55°.

Leaves:
- *Bud*.—Length: 2.0 mm. Diameter: 1.0 mm. Color: 200D.

*Overall size*.—Large.
*Length*.—15.0 cm.
*Width*.—6.0 cm.
*Surface texture*.—Wrinkled.
*Form*.—Broad; elliptic.
*Color*.—Both surfaces: About 137A to 138A (Occasional reddish tinge).
*Mid-vein*.—Size: Medium. Color: Light pink.
*Petiole*.—Length: 2.5 cm. Thickness: 1.0 mm to 1.5 mm. Color: Greenish with pinkish overtones.
*Leaf glands*.—Absent.
*Stipules*.—Shape: Round. Size: Up to 2.0 cm. Color: Green.

Flowers:
*Bloom time*.—Flowers reach full bloom in the first week of April and last approximately 10 days.
*Size*.—Large; Approximately 30.0 mm to 35.0 mm.
*Color*.—Usually white with light pink base; overall effect at a distance is light pink.
*Number*.—2 to 3 flowers per cluster.
*Fragrance*.—None.

Petals:
*Number*.—5 per flower.
*Length*.—15.0 mm.
*Width*.—Widest point is 12 mm; the base and apex are both 10 mm.
*Shape*.—Ovoid.
*Margin*.—Entire, with a forked split at the tip.
*Texture*.—Smooth.
*Appearance*.—Petals overlap.
*Color* (*both surfaces*).—155C background with 10% of the petal having 66D at the base in a fan shape.

Sepals:
*Shape*.—Triangular.
*Margin*.—Entire.
*Texture*.—Smooth.
*Length*.—5.0 mm.
*Width*.—2.0 mm.
*Color* (*both surfaces*).—138A.

Reproductive organs:
*Stamens*.—Number (per flower): 27. Filament length: 3.0 mm. Anthers: Shape: Round. Length: Less than 1.0 mm. Color: 26A. Pollen: Color: 21A. Amount: Light.
*Pistils*.—Length: 4.0 mm. Style: Length: 4.0 mm. Color: 145C. Stigma: Shape: Round. Color: 144A.

Fruit:
*Size*.—Small.
*Axial diameter* (*average*).—0.8 cm.
*Axial diameter transverse in the suture plane*.—0.7 cm.
*Axial diameter transverse and at a right angle to the suture plane*.—0.8 cm.
*Shape*.—Symmetric.
*Stem cavity*.—Shape: Round. Depth: Small. Breadth: Narrow.
*Base shape*.—Round.
*Apex shape*.—Round.
*Skin*.—Thickness: Thin. Texture: Tender. Color: Black-violet.
*Flesh*.—Texture: Tender. Juice: Dark red.
*Aroma*.—Absent.
*Flavor*.—Bitter.
*Use*.—Not recommended for eating.

Soil Adaptation and Tolerance
Wet soil: Resilient.
Cold temperatures: Hardy to Zone 4.
Drought: Tolerant.
Asphixia: Tolerant.
Multiplication Ability
Layering: Weak propagation.
Hardwood cuttings: Resistant to no propagation.
Softwood cuttings: Great propagation.
Pathogen Resistance
Fungal disease: Tolerant.
Insects: Not resistant.
Mites: Weak resistance.
Viruses: Tolerant.
Diseases: Tolerant to *Coccomyces* and *Verticillium*; sensitive to *Agrobacterium*.
Root-knot nematodes: Susceptible; galls do not form, but nematode reproduces well.
Lesion nematodes: Moderately resistant.
Performance as a Rootstock When Grafted
Root sprouts (suckering): Suckers (shoots that grow from the rootstock and disrupt the growth of the scion) are not present.
Anchorage: Very good.
Compatibility: Compatible with all varieties of sweet and sour cherry varieties known to the breeder.
Vigor: Medium; displaying fast growth in hot conditions.

I claim:

1. A new and distinct variety of *Prunus* sp. plant, as illustrated and described.

* * * * *